United States Patent

Zanotti et al.

[11] Patent Number: 6,096,188
[45] Date of Patent: Aug. 1, 2000

[54] ANTI-AGING ADDITIVE COMPOSITION FOR A QUENCH OIL CIRCUIT IN AN ETHYLENE PRODUCTION PLANT AND METHOD OF OPERATING THE CIRCUIT

[75] Inventors: Andrea Zanotti; Francesco Magri'; Roberto Faina, all of Rome, Italy

[73] Assignee: Chimec S.p.A., Rome, Italy

[21] Appl. No.: 09/162,212

[22] Filed: Sep. 30, 1998

[30] Foreign Application Priority Data

Oct. 6, 1997 [IT] Italy ................ RM97A0598

[51] Int. Cl.[7] ........................ C07C 7/20
[52] U.S. Cl. ............... 208/48 Q; 208/48 AA; 585/648; 585/650
[58] Field of Search .............. 208/48 AA, 48 Q; 585/648, 650

[56] References Cited

U.S. PATENT DOCUMENTS

| 2,951,029 | 8/1960 | Johnston et al. . | |
| 4,929,778 | 5/1990 | Roling . | |
| 5,824,829 | 10/1998 | Maeda et al. | 585/3 |

FOREIGN PATENT DOCUMENTS

| 0230366 | 7/1987 | European Pat. Off. . |
| 0467848 | 1/1992 | European Pat. Off. . |
| 0818524 | 1/1998 | European Pat. Off. . |
| 595916 | 12/1947 | United Kingdom . |

OTHER PUBLICATIONS

XP-002090468, Sheremeta et al., Chemical Abstract, vol. 101, No. 10, (1984).
XP-002090470, Database WPI, Derwent Publications Ltd., London, GB.
XP-0020904741, Database WPI, Derwent Publications Ltd., London, GB.
XP-002090472, Database WPI, Derwent Publications Ltd., London GB.
XP-002090469, Ionescu et al., Chemical Abstracts, vol. 88, No. 24, (1978).

*Primary Examiner*—Bekir L. Yildirim
*Attorney, Agent, or Firm*—Browdy and Neimark, P.L.L.C.

[57] ABSTRACT

An anti-aging additive composition and an operating method to control the quench oil viscosity in an ethylene production plant are described, capable of raising the yield of said plant through a control of the quench oil viscosity related to a significant increase in the operation temperature of the plant fractionating column, said composition comprising an effective quantity with respect to the aging of said oil of at least one component selected in the group constituted by alkylated phenols, alkylated biphenols, diphenols, alkylated diphenols, aromatic amines and nitroxides, precursors and mixtures thereof.

15 Claims, 1 Drawing Sheet

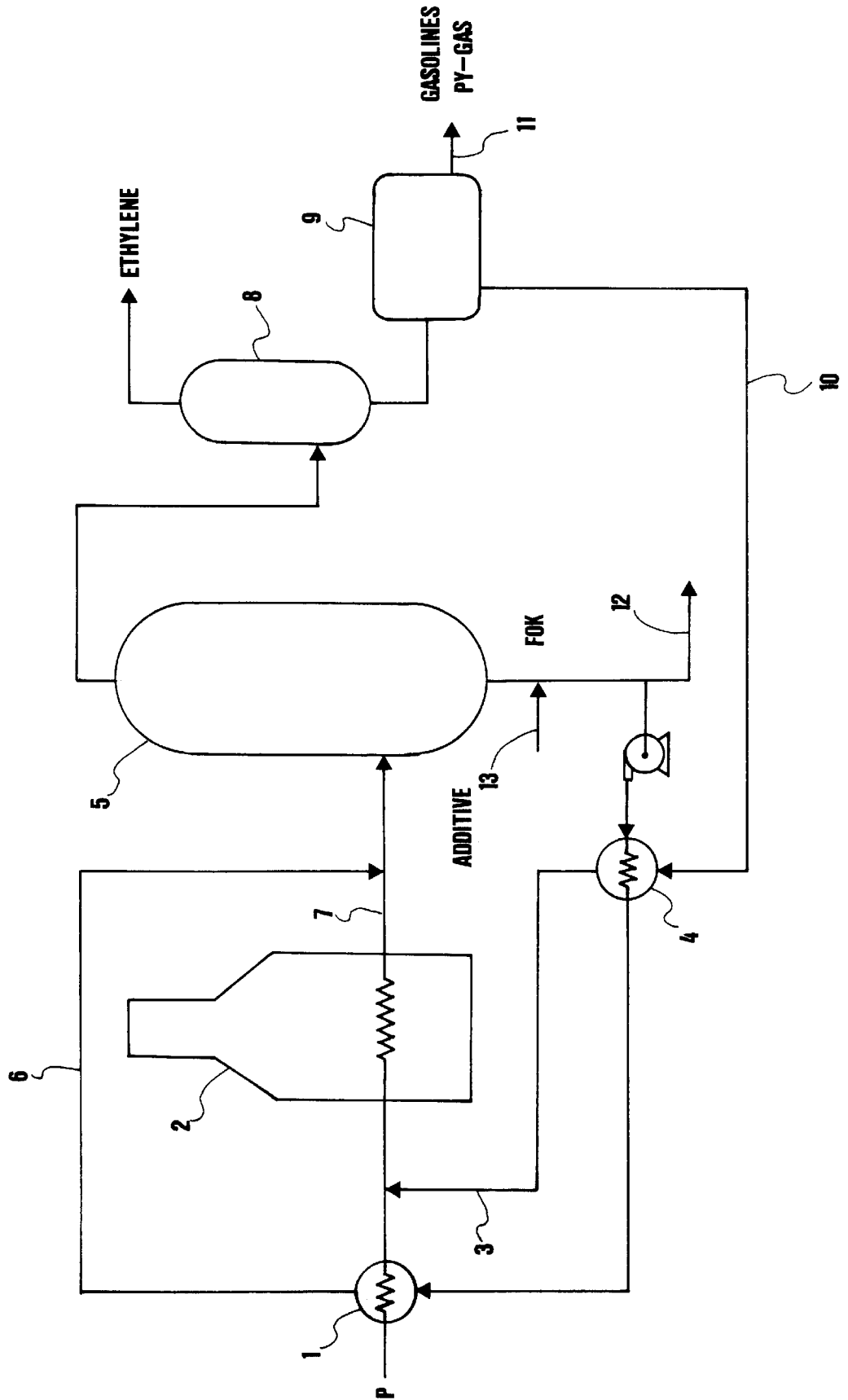

ANTI-AGING ADDITIVE COMPOSITION FOR A QUENCH OIL CIRCUIT IN AN ETHYLENE PRODUCTION PLANT AND METHOD OF OPERATING THE CIRCUIT

BACKGROUND OF THE INVENTION

1. Field of the Invention

The present invention relates to an anti-aging additive composition for a quench oil circuit in an ethylene production plant, specifically to control the viscosity of the quench oil (FOK) obtained as bottom product of the fractionating column, and utilized for steam production in the gasifying cracking process to cool down the output from the cracking, and for the commercial production of fuel oil (FOK).

2. Description of the Prior Art

As it is well known, ethylene production for petrochemical use is an important process in the field of oil refinery.

This production takes place in different steps, starting from an ethane, virgin naphtha or gas oil feed, that is subject to gasifying cracking, by means of high temperature steam injection, in a reactor where temperatures reach values in the range of 750–900° C.

This output is cooled by mixing it with a colder fluid and fed in a fractionating column where the separation of ethylene and light gasolines from a heavier oil (FOK) takes place.

The quality of the distillation, i.e. the amount of ethylene, light olefins and gasolines extracted from the top of the column, is influenced by the temperature of the feed in the fractionating column. A higher temperature results in a higher yield of light products.

The so-called quench oil is utilized as fluid, that is the heavy oil extracted from the bottom of the fractionating column, marketable as fuel oil.

An amount of the quench oil is extracted to be used as fuel, while the remaining part is cooled by utilizing it for the process steam production and for a preheating of the crude charge.

As a consequence of cooling, the oil reaches a temperature of about 100–170° C. and it is mixed at a 8:1 ratio with the fractionating column feed in order to cool the latter.

The resulting temperature at the inlet of the fractionating column is between about 170° C. and 220° C.

Even though an increase of this temperature is desirable for its cost-effectiveness, nevertheless it presents a number of serious unfavorable side effects, showing up particularly as a viscosity increase of the quench oil injected into the cycle.

In fact, the continually recirculating quench oil remains in the circuit at relatively high temperatures for long periods of time, and this causes its aging, because of the presence of unsaturated compounds, with polymers and rubbers formation and a resulting viscosity increase.

All the aforementioned side effects obviously entail negative repercussions on the functioning of the production plant. These are the increase of the power required by the recirculation pumps, the reduction of the thermal exchange coefficients involved in steam production, reduction that compensates and outdoes a possible contribution provided by the temperature increase, and the increase of the maintenance costs involved in the cleaning of the plant components exposed to the quench oil.

In order to avoid the aforementioned side effects, the conventional plant is operated maintaining a quench oil temperature that enables its viscosity not to overstep a value that ensures the plant operational safety. In order to avoid the occurrence of the aforementioned side effects, the conventional plant is operated maintaining a quench oil temperature so that its viscosity does not exceed a value ensuring the operational safety of the plant.

Contrary to that, an operation temperature rise in the fractionating column would make it possible to obtain a higher production of steam, as well as a higher recovery of light products, with an ensuing increase of the plant global efficiency.

SUMMARY OF THE INVENTION

The technical problem underlying the present invention is that of providing an additive composition of the quench oil enabling the minimization of the drawbacks mentioned with reference to the state of the art, in order to increase the ethylene production plant efficiency.

This problem is solved by an anti-aging additive composition that constitutes the subject-matter of this invention, comprising an effective quantity with respect to the aging of the said oil, of at least one component selected in a group constituted by alkylated phenols, alkylated biphenols, diphenols, alkylated diphenols, aromatic amines and nitroxides, precursors and mixtures thereof.

The main advantage of the additive according to this invention lies in enabling a quench oil viscosity control in view of a significant rise of the fractionating column operation temperature.

Another technical problem associated with the one mentioned above, concerns the control rules for the plant operations of an ethylene production plant that utilizes quench oil to cool the feed at the fractionating column.

Therefore, the present invention in addition relates to a method for operating the circuit as specified above, said method comprising the following steps:

drawing a quench oil sample from the bottom of said fractionating column operating at a predetermined operation temperature;

measuring said quench oil viscosity;

adding to the oil flow of the quench oil circuit a quantity of additive according to the invention, selected accordingly to the measured value of said quench oil viscosity;

testing the circuit oil viscosity response to the adding of said quantity of additive, at said predetermined operation temperature; and increasing said operation temperature until increasing again at said measured value said quench oil viscosity.

BRIEF DESCRIPTION OF THE DRAWING

In order to better understand the invention aspects, the only FIGURE of the annexed drawing shows schematically and in a simplified way an ethylene production plant.

DESCRIPTION OF THE PREFERRED EMBODIMENT

The P feed of ethane, virgin naphtha or gas oil is preheated in a counterflow heat exchanger 1 by the quench oil flow, and fed into a steam cracking reactor 2, together with a steam flow 3. This steam flow is produced in a steam generator 4, exploiting the heat, at about 160–170° C., of the oil delivered from a fractionating column 5.

The oil flow 6, cooled down at about 100–170° C. by passing through the heat exchanger 1 and the steam generator 4, is mixed with the crackerized flow 7, coming out of reactor 2 at about 850° C., so as to bring it rapidly to an inlet temperature of about 160° C. at the fractionating column 5.

The bottom product of the latter, constituting quench oil (FOK), is sent to the steam generator 4 for the steam production.

The top product, constituted by ethylene, steam and gasolines, goes into a flash tower 8 for the separation of ethylene as final product.

The remaining top product (water and gasolines) goes into a separator 9 for the recovery of water that is directed to the steam generator 4 through the pipe 10, as well as for the recovery of gasoline and py-gas as product 11. Quench oil in excess with respect to the plant cycle needs is also extracted as fuel oil (FOK), indicated 12.

As alkylated phenols are mentioned for instance those alkylated in position 2 and/or 4 and/or 6, as 2,6-di-ter.butyl-phenol; 2,4-dimethyl,6-ter.butyl-phenol; 2,6-di-ter.butyl-4-methyl-6-nonyl-phenol and similar.

As alkylated biphenols are mentioned for instance 4,4'-methylene-bis-(2,6-di-ter.butyl,4-methyl-phenol and similar.

As diphenols are mentioned for instance catechol, hydroquinone and 4-ter.butyl catechol and similar.

As aromatic amines can be mentioned for instance N,N'-di-sec.butyl-p-phenylendiamine; N-aryl,N'alkyl-p-phenylen diamines and so on.

As nitroxides are mentioned for instance 4-hydroxi-2,2,6,6-tetramethyl-piperidin-nitroxide; 1-piperidinyloxi, 4,4'-(1,10-dioxi-1-10-decanedyl) bis(2,2,6,6 tetramethyl) and similar.

The additive according to the invention is injected, as indicated by 13, in the quench oil circuit in a predetermined amount between the bottom of the fractionating column and the recirculating pump.

According to a more general aspect of the invention, the additive is injected in an amount between 20 ppm and 200 ppm, depending on the quench oil flow rate.

Such an amount is preferably higher than 50 ppm in order to maintain the viscosity values, under the same operational temperature, far below the predetermined safety limits.

For instance, said operative viscosity values can be in the order of 15 cst with respect to a safety limit of 25 cst.

When the predetermined amount is between 100 ppm and 120 ppm, a bottom column temperature of up to 15° C. higher than the usual value of 160–210° C. can be advantageously obtained, without relevant promoted aging phenomena and the subsequent sudden viscosity increase.

Under the same conditions of exchange surfaces and recirculating power, such a temperature yields a higher quantity of steam to be mixed to the naphtha feed.

Moreover, the amount of the light products obtained from the top of the fractionating column is sensibly increased, with a consequent increase in cost-effectiveness in the refining process.

As it is known, the operation of a quench oil-utilizing ethylene production plant is subject to extremely delicate balance conditions. Actually, in the presence of determining conditions, oil aging proceeds at exponential rate. This makes continuous monitoring and prompt and precise interventions unavoidable.

The increasing of the operation temperature of the fractionating column as an effect of the additive utilization according to the invention, is therefore a problem which may find its solution, but the search for this solution is an awkward, not danger-free issue, because of the aforementioned reasons.

The operating method according to the invention solves this problem.

In fact, it has been noted that a direct relation exists between an oil viscosity measure, carried out for instance by closed container method, and the real behavior of the oil inside the quench circuit, with reference to its real viscosity.

This allows a measuring to be done on oil samples obtained directly from the inside of the plant, depending on the adding of determined additive amounts according to the invention, that are thus variable both with respect to the oil charge fed into the plant, and to temperature and time. Those tests, carried out during the plant operation, allow an adequate forecast at the additive kind and amount that has to be added in order to obtain the object of increasing the operation temperature, compatibly with keeping flow viscosity within a safety limit value.

Specifically, a fuel oil drawing is carried out, with subsequent subdivision in samples.

Then a comparative test of aging is carried out inside the closed container, at a predetermined temperature, and for a predetermined time interval.

For instance, oil aging is obtained at 205° C. for 24 hours. Before and after aging, viscosity and the so-called pour point are measured at a predetermined temperature (e.g. of 90° C.).

Viscosity is measured according to the ASTM D445 method, and the pour point is measured according to the ASTM D97 method.

The test is to be carried out on different samples, adding a preset amount of additive, e.g. between 10 ppm and 50 ppm, to some of them.

Another test can be carried out by subjecting the samples to a viscosity measuring at 50° C., for example by the aforementioned method, after extraction and after aging cycles e.g. of 24 and 120 hours at 185° C., after adding the predetermined additive dosage.

Once those tests are carried out it is possible to accomplish the aforementioned operating method, wherein a quench oil viscosity measurement is carried out at a predetermined operation temperature, in order to keep said viscosity within a safety limit value, e.g. of 20 cst.

An amount of additive according to this invention is then added to the quench oil flow coming out of the bottom of the fractionating column, amount which can be obviously presumed from said quench oil viscosity value.

Said amount is represented e.g. by a 100 ppm dosage.

The oil viscosity response to the adding of said additive amount is then tested at the aforementioned predetermined operation temperature. This test will show a significant quench oil viscosity decrease.

Said operation temperature can now be increased, until the viscosity of said quench oil is raised to the predetermined reference value. This reference value can be, for example, equal to a safety value of 20 cst.

Some examples of additive application according to this invention will be disclosed hereinafter, given by way of explanation, and not for limitative purposes.

EXAMPLE 1

In an ethylene production plant, some fuel oil samples were extracted from the bottom of the fractionating column.

Viscosity at 50° C. was measured by using CANNON FESKE (ASTM D445) viscosimeters, and resulted to be equal to 100 centipoise (cps).

An additive containing 4,4'-methylene-bis-(2,6-di-ter.butylphenol) and catechol in a 1:1 ratio with a 30 ppm dosage was added to the two samples.

A first sample underwent aging at 185° C. for 24 h in a closed steel container. A second sample underwent aging at 185° C. for 120 h in an analogous container.

A third and a fourth sample, with no added additives, were aged with the same parameters of respectively the first and the second sample, always in a closed container.

Finally, viscosity's at 50° C. were measured as described above, obtaining the following results

TABLE 1

|  | 185° C./24 h | 185° C./120 h |
| --- | --- | --- |
| without additive | 200 cps | 450 cps |
| with additive | 176 cps | 372 cps |

As it can be noted, the difference between viscosity's detected in samples with and without the additive increases in percentage with the lengthening of the aging time.

The aforementioned additive was added to the oil flow of said plant with a 100 ppm dosage. Within 24 hours, the following was evidenced:

TABLE 2

|  | before | after |
| --- | --- | --- |
| Temperature (° C.) | 177.9 | 176.7 |
| Viscosity (centistoke - cst) | 20.1 | 15.1 |

As it can be noted, a relevant difference in viscosity was obtained, compared to a negligible temperature decrease.

This additive addition allowed an operation temperature (always relative to the bottom of the fractionating column) of 185° C., with a viscosity level at 190° C. of the order of 20 cst, compared to the 178° C. obtained without additive.

EXAMPLE 2

In an ethylene production plant, some fuel oil samples were extracted from the bottom of the fractionating column. Viscosity was measured with the aforementioned method, at 50° C., resulting equal to 100 centipoise (cps).

An additive containing 2,4-dimethyl-6-ter.butyl phenol and 4-ter.butyl catechol in a 2:5 ratio with a 30 ppm dosage was added to two samples.

A first sample underwent aging at 185° C. for 24 h; a second sample underwent aging at 185° C. for 120 h.

A third and a fourth sample, with no added additives, were aged with the same parameters of respectively the first and the second sample.

All the agings, as for example 1, took place in a closed steel container.

At the end, viscosity's at 50° C. were measured as described above, obtaining the following results:

TABLE 3

|  | 185° C./24 h | 185° C./120 h |
| --- | --- | --- |
| without additive | 200 cps | 450 cps |
| with additive | 145 cps | 315 cps |

Also in this case, as it can be seen, the difference between viscosity's detected in samples with and without the additive increases in percentage with the lengthening of the aging time.

Viscosity at 90° C. and pour point were measured in four new samples of the same origin. Then they were aged at 205° C. for 24 h in a closed container. A sample was left without additive, while additive was added to the other three samples with a dosage of respectively 15 ppm, 30 ppm, 45 ppm.

Finally, viscosity and pour point at 50° C. were measured as described above, obtaining the following results:

TABLE 4

|  | Viscosity at 90° C. (cps) | pour point (° C.) |
| --- | --- | --- |
| not aged | 40 | −21.0 |
| aged (without additive) | 825 | +16.2 |
| aged (15 ppm) | 722 | +14.5 |
| aged (30 ppm) | 600 | +13.4 |
| aged (45 ppm) | 500 | +12.2 |

The effects of the additive tested on fuel oil viscosity and pour point can be easily observed.

The aforementioned additive was added to the oil flow in the plant at issue with a 100 ppm dosage, and a global viscosity decrease of 30% was detected.

In this case, the additive addition made it possible to increase the operation temperature by 5–7° C., keeping circuit viscosity unchanged (lower than 20 cst at 90° C.).

EXAMPLE 3

In an ethylene production plant, some fuel oil samples were extracted from the bottom of the fractionating column.

Viscosity at 90° C. and pour point were measured with the aforementioned methods. Then they were aged at 205° C. for 24 h in a closed steel container.

A sample, indicated with A, was left without any additive. To two samples, indicated with B and C respectively, an additive was added, containing 2,4-dimethyl-6-ter.butyl phenol and 4-ter.butyl catechol in a 2:5 ratio with a dosage of respectively 20 ppm (B) and of 35 ppm (C).

To two other samples, indicated with D and E, respectively, an additive containing 2,4-dimethyl-6-ter.butyl phenol and (1-piperidinyloxy,4,4'-((1,10-dioxo-1-10 decanedyl)bis (2,2,6,6-tetramethyl-) in a 2:5 ratio with a 20 ppm (D) and a 35 ppm (E), respectively, was added.

Finally, viscosity's and pour point were measured according to ASTM as described above, obtaining the following results:

TABLE 5

| | Viscosity at 90° C. (cps) | Pour point (° C.) |
|---|---|---|
| not aged | 4.85 | −27.5 |
| aged A | 22.2 | −24.0 |
| aged B | 19.0 | −25.8 |
| aged C | 15.9 | −27.1 |
| aged D | 18.2 | −25.6 |
| aged E | 15.9 | −27.2 |

Also in this case, the effects of the additive tested on extracted fuel oil viscosity and pour point can be easily observed.

EXAMPLE 4

Also the other compounds mentioned below were tested by aging in a closed container.

Extracted fuel oil samples show a 100 cps viscosity at 50° C. Aging tests at 185° C. for 24 h and 120 h were carried out on samples with no additives and on samples treated with a 30 ppm additive dosage as to table 6. Viscosity at 50° C. was then measured as aforesaid described. Results are as follows:

TABLE 6

| (viscosity in cps) | 24 h | 120 h |
|---|---|---|
| without additive | 200 | 450 |
| 2,4- dimethyl, 6-ter.butyl-phenol | 195 | 420 |
| catechol | 160 | 330 |
| 2,2'- methylene-bis (4-methyl-6-nonylphenol) | 174 | 400 |
| 4-ter.butyl catechol | 150 | 320 |
| catechol + 4-ter.butyl catechol | 145 | 320 |
| 2,4-dimethyl,6-ter.butyl-phenol + N,N'-di-sec.butyl-p-phenylendiamine | 195 | 352 |

As it can be seen, the trend of all the tested additives is that of promoting the lowering viscosity with the progression of aging.

For instance, in this case the additives can be used according to the invention.

A man skilled in the art will be able to carry out several further modifications to the anti-aging additive composition described above, without departing thereby from the protective scope of the invention as defined by the following claims.

What is claimed is:

1. Method for operating an ethylene production plant utilizing oil, obtained as bottom product of the fractionating column, for steam production in the gasifying cracking process, in order to cool down the cracked flow exiting from the gasifying cracking reactor at the fractioning column, and wherein said oil is kept at a predetermined reference value of viscosity based on a plant safety level, said method comprising:

drawing a quench oil sample at the bottom of said fractionating column operating from a predetermined operation temperature;

measuring of the oil viscosity;

adding to the oil flow of the quench oil circuit an amount of an anti-aging additive consisting of an effective quantity, with respect to said oil flow, of at least one component selected from the group consisting of alkylated phenols, alkylated biphenols, diphenols, alkylated diphenols, aromatic amines and nitroxides, precursors and mixtures thereof, selected accordingly to the measured value of said quench oil viscosity;

testing the circuit oil viscosity response to the adding Of said amount of additive, at said predetermined operation temperature; and increasing said operation temperature until said quench oil viscosity has increased to said predetermined reference value of viscosity.

2. Method according to claim 1, wherein said component comprises at least one alkylated phenol having alkylation in one or more of the positions 2, 4 or 6.

3. Method according to claim 2, wherein said at least one alkylated phenol is 2,6-di-ter.butyl-phenol, 2,4-dimethyl,6-ter.butyl-phenol, 2,6-di-ter.butyl,4-methyl-phenol, or mixtures thereof.

4. Method according to claim 1, wherein said at least one alkylated biphenol is 4,4'-methylene-bis-(2,6-di-ter.butylphenol), 2,2'-methylene-bis(4-methyl-6-nonyl), or mixtures thereof.

5. Method according to claim 1, wherein said component comprises at least one alkylated diphenol selected from the group consisting of catechol, hydroquinone, 4-ter.butyl-catechol, and mixtures thereof.

6. Method according to claim 1, wherein said component comprises at least one aromatic amine selected from the group consisting of N,N'-di-sec.butyl-p-phenylendiamine, N-aryl,N'-alkyl-p-phenylendiamines, and mixtures thereof.

7. Method according to claim 1, wherein said component comprises at least one nitroxide selected from the group consisting of 4-hydroxy-2,2,6,6-tetramethyl-piperidin-nitroxide, 1-pipe ridiniloxy,4,4'-(1,10-dioxo-1,10-decylenedyl)bis(2,2,6,6-tetramethyl), and mixtures thereof.

8. Method according to claim 1, wherein said anti-aging additive composition comprises 4,4'-methylene-bis-(2,6-di-ter.butyl-phenol) and catechol in a ratio of about 1:1.

9. Method according to claim 1, wherein said anti-aging additive composition comprises 2,4-dimethyl-6-ter.butyl-phenol and 4-ter.butyl-catechol in a ratio of about 2:5.

10. Method according to claim 1, wherein said anti-aging dditive composition comprises 2,4-dimethyl-6-ter.butyl-phenol and 4,4'-(1,10-dioxo-1,10-decylenedyl)bis(2,2,6,6-tetramethyl) in a ratio of about 2:5.

11. Method according to claim 1, wherein said anti-aging additive composition comprises 2,4-dimethyl-6-ter.butyl-phenol and N,N'-di-sec.butyl-p-phenylendiamine.

12. Method according to claim 1, wherein said anti-aging additive composition comprises catechol and 4-ter.butyl-catechol.

13. Method according to claim 1, wherein said effective quantity is between 20 ppm and 200 ppm.

14. Method according to claim 13, wherein said effective quantity is not less than 50 ppm.

15. Method according to claim 14, wherein said effective quantity is between 100 ppm and 120 ppm.

* * * * *